United States Patent
Pathi et al.

(10) Patent No.: US 7,638,633 B2
(45) Date of Patent: Dec. 29, 2009

(54) PROCESS FOR SYNTHESIS OF PROTON PUMP INHIBITORS

(75) Inventors: Srinivas Laxminarayan Pathi, Karnataka (IN); Rajendra Narayanrao Kankan, Maharashtra (IN); Dharmaraj Ramachandra Rao, Maharashtra (IN)

(73) Assignee: Cipla Limited, Maharashatra (IN)

( * ) Notice: Subject to any disclaimer, the term of this patent is extended or adjusted under 35 U.S.C. 154(b) by 0 days.

(21) Appl. No.: 11/816,604

(22) PCT Filed: Feb. 21, 2006

(86) PCT No.: PCT/IN2006/000077

§ 371 (c)(1), (2), (4) Date: Aug. 17, 2007

(87) PCT Pub. No.: WO2006/117802

PCT Pub. Date: Nov. 9, 2006

(65) Prior Publication Data

US 2008/0161579 A1    Jul. 3, 2008

(30) Foreign Application Priority Data

Feb. 21, 2005    (IN) .................................. 190/2005

(51) Int. Cl.
*C07D 401/12* (2006.01)

(52) U.S. Cl. .................................................. 546/273.7
(58) Field of Classification Search ............... 546/273.7
See application file for complete search history.

(56) References Cited

FOREIGN PATENT DOCUMENTS

| EP | 0268956 A | 6/1988 |
|---|---|---|
| WO | WO/01/04109 | 1/2001 |
| WO | WO/2004/063188 A | 7/2004 |

OTHER PUBLICATIONS

PCT International Search Report for CIPLA Limited, et al., International Application No. PCT/IN2006/000077. Filed Feb. 21, 2006, Dated Oct. 3, 2006.
PCT International Preliminary Report on Patentability for CIPLA Limited, et al., International Application No. PCT/IN2006/000077. Filed Feb. 21, 2006, Dated Jul. 19, 2007.
Anonymous, Aug. 25, 2005, "Sodium Rebaprazole Preparation", IP.com Journal, 5(9A): 20-21 (No. IPCOM000127347D).

*Primary Examiner*—Patricia L Morris
(74) *Attorney, Agent, or Firm*—Law Offices of Albert Wai-Kit Chan, PLLC

(57) ABSTRACT

A process for preparation of rabeprazole sodium comprising oxidation of wet or dry rabeprazole sulphide with sodium hypohalite in water or a mixture of water and water miscible solvent using alkali metal hydroxide and catalyst is disclosed herein. The present invention also discloses process for preparation of rabeprazole sulphide.

10 Claims, No Drawings

US 7,638,633 B2

PROCESS FOR SYNTHESIS OF PROTON PUMP INHIBITORS

This application is the National Stage of International Application No. PCT/IN2006/000077, filed Feb. 21, 2006, which claims priority of Indian Application No. 190/MUM/2005, filed Feb. 21, 2005, the entire disclosures of the preceding applications are incorporated by reference herein in its entirety.

TECHNICAL FIELD OF THE INVENTION

The present invention relates to an improved, cost effective, environmental friendly process for preparation of Rabeprazole sodium (2-[[[4-(3-methoxypropoxy)-3-methyl-2-pyridinyl]methyl]sulfinyl]1H-benzimidazole sodium).

BACKGROUND OF THE INVENTION

Rabeprazole sodium is a proton pump inhibitor which can produce profound and sustained inhibition of gastric acid secretion with responses of Proton pump inhibitors being more rapid when compared with other anti-secretory drugs. Proton pump inhibitors work by inhibiting the production of stomach acid, by shutting down a system in the stomach known as proton pump (Hydrogen-Potassium adenosine triphosphate enzyme system).

EP0268956 A2 and WO01/04109 have disclosed the preparation of rabeprazol sodium. It describes the synthesis of rabeprazole sulphide, rabeprazole base and its sodium salt. Rabeprazole sulphide (2-[{4-(3-methoxy propoxy)-3-methyl pyridine-2-yl}methyl thio]-1H-benzimidazole) is prepared by condensation of 2-chloromethyl-4-[3-methoxy propoxy]-3-methylpyridine and 2-mercapto benzimidazole in ethanol by using sodium hydroxide. This mixture is stirred at 50° C. for 3 hours. The solvent is distilled to obtain residue which is further purified by column chromatography using silica gel.

Rabeprazole is prepared by oxidizing 2-[{4-(3-methoxy propoxy)-3-methyl pyridine-2-yl}methyl thio]-1H-benzimidazole with m-Chloroperbenzoic acid to afford the Rabeprazole base which is further converted to its sodium salt by using 0.1 N aqueous solution of Sodium hydroxide, followed by addition of ethanol. The water is removed by azeotropic distillation and the product is precipitated by using ether as solvent. The disadvantage of this process is the presence of higher residual solvent content in the product resulting in lower potency. This method is not suitable for industrial scale preparation of rabeprazole sodium.

WO 02/062786 discloses a process for preparation of Rabeprazole substantially free of a sulphone by-product wherein the oxidation is carried out using tertiary butyl hydroperoxide in the presence of vanadyl bis-acetyl acetonate catalyst.

PCT Application PCT/GB2004/000064 and International Publication Number WO 2004/063188 A1, discloses the preparation of rabeprazole and benzimidazole type of compounds. Accordingly, rabeprazole base is prepared by oxidation using sodium hypohalites and isolated. Rabeprazole sodium is prepared by dissolving rabeprazole base in ethylacetate and methanolic ammonia mixture to which methanolic sodium hydroxide is added. The solvent is distilled and rabeprazole sodium is isolated from ethylacetate and n-heptane/n-hexane mixture.

These prior art processes cited above have many disadvantages and are not ideally suited for industrial application. These processes involve use of expensive solvent and hazardous oxidizing reagents. Further the isolation procedure described in the prior art involves azeotropic distillation of water during which the product is exposed to high temperature and leads to certain impurities.

The related prior art process also involves use ether which is not suited for large scale production. Further, purification of the final product in prior art is done by column chromatography which also is a not an industrially viable process.

Further the conversion of rabeprazole base to its sodium salt is a multiple step process, which involves isolation, purification and drying of the intermediates used.

OBJECT OF THE INVENTION

The object of the present invention is to provide an efficient, industrially and environmentally safe process for the synthesis of rabeprazole sodium, by overcoming the shortcoming of the earlier process described in the prior art. Another object of the present invention is to prepare raberazole sodium without the isolation of rabeprazole base.

Yet another object of the present invention is to provide a process for the synthesis of rabeprazole sulfide in an aqueous media.

SUMMARY OF THE INVENTION

The present invention discloses a process for preparation of rabeprazole sodium comprising oxidation of wet or dry rabeprazole sulphide with sodium hypohalite in water or a mixture of water and water miscible solvent using alkali metal hydroxide and catalyst. The present invention also discloses process for preparation of rabeprazole sulphide.

DETAILED DESCRIPTION OF THE INVENTION

The present invention aims at providing an improved and environmental friendly (ecofriendly) process for the preparation of rabeprazole sulfide (2-[[[4-(3-methoxy-propoxy) 3-methyl-2-pyridinyl]methyl]-thio]-1H benzimidazole), preferably using an inexpensive and readily available reagent, by use of Green Chemistry i.e., avoid or minimize use of organic solvents that will enable commercial production to be more profitable, less wasteful, less damaging to the environment.

The present invention also provides a method of treating gastric ulcers and related conditions, which comprises administering to a patient in need of such treatment rabeprazole sodium prepared by a process substantially as hereinbefore described.

In one aspect, the present invention describes process for the preparation of rabeprazole sulphide (II) by condensation of compound of formula (III) with compound of formula (IV), the condensation is carried out in water or a mixture of water and water miscible solvent like C1-C4 alcohols, ketones, preferably acetone, nitrites preferably acetonitrile in the presence of an alkali metal hydroxide, preferably sodium Hydroxide.

Typically the condensation reaction is carried out at a temperature between 10° C. to 60° C., preferably between 15° C. to 30° C.

According to another aspect of the present invention, the thiol compound of formula (II) is isolated by direct filtration and does not involve any distillation or workup procedures and also does not make use of unit operations of drying, milling for the subsequent oxidation step.

Another aspect of the present invention provides a process for preparation of rabeprazole sodium (2-[[[4-(3-methoxy-propoxy) 3-methyl-2-pyridinyl]methyl]-sulfinyl]-1H benzimidazole sodium) of formula (I) wherein oxidation of wet or dry rabeprazole sulfide 2-[[[4-(3-methoxy-propoxy) 3-methyl-2-pyridinyl]methyl]-thio]-1H benzimidazole of formula (II) is carried out in water or a mixture of water and water miscible solvent, using an oxidizing agents like sodium hypohalites in presence of an alkali metal hydroxides like sodium hydroxide and a catalytic agent like pyridine. The reaction is carried at a temperature between −10° C. to 60° C. preferably between 0° C. to 20° C., after completion of the reaction the reaction mass is saturated by using inorganic saturating agents, further the sodium salt is extracted using water immiscible organic solvents. The solvent is then removed by distillation, the residue is dissolved in another organic solvent and the sodium salt of formula (I) is precipitated using an antisolvent. The product is filtered and dried under vacuum

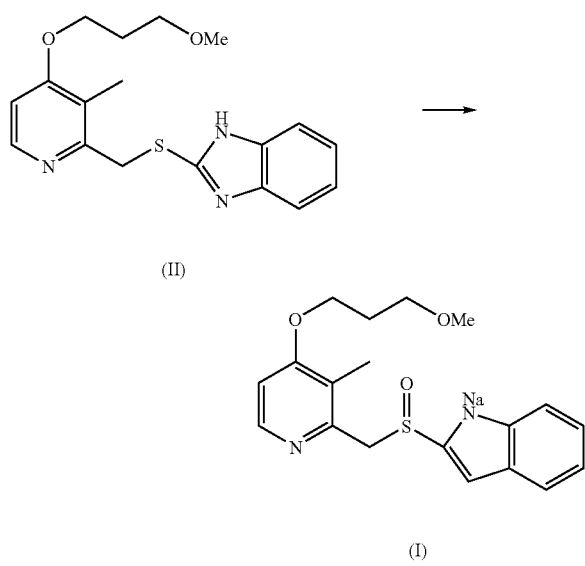

Another aspect of the present invention, is to provide a process for the preparation of Rabeprazole sulphide 2-[[[4-(3-methoxy propoxy)-3-methyl-2-pyridinyl]methyl]thio]-1H benzimidazole of formula (II) in which 2-mercapto benzimidazole of formula (IV) is condensed with 2-Chloromethyl-4-(3-methoxy propoxy)-3-methylpyridine hydrochloride of formula (III) in water or a mixture of water and water miscible solvent in presence of alkali metal hydroxide. The condensation is carried at temperature range between 10° C. to 60° C., preferably between 15° C. to 30° C. and isolation of the compound of formula (II).

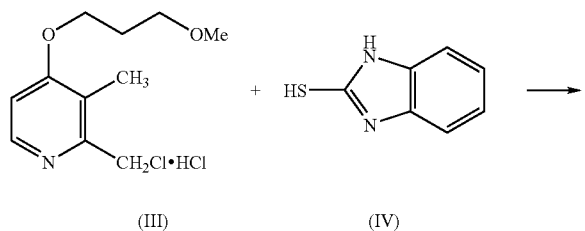

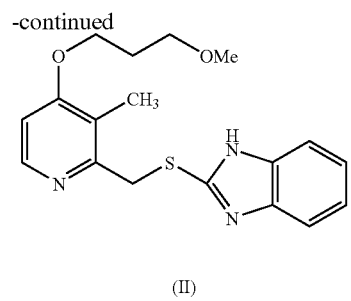

In another aspect of the present invention, the oxidation is carried out in the presence of a catalyst suitably selected from the group consisting of pyridine, diisopropyl ethyl amine and N,N dimethyl amino pyridine. The use of such a catalyst is desirable to avoid further formation of undesirable byproducts.

Typically, a process according to the present invention comprises suspending rabeprazole sulphide in water or mixture of water and water miscible solvents like C1-C4 alcohols, acetone, acetonitrile, preferably water which makes use of 0.5 to 5% of alkali metal hydroxide, preferably sodium hydroxide solution.

Further in the present invention, the oxidizing agent used is an aqueous hypohalite solution having a concentration in the range of 2.0% to 5.0% (1.0-2.0 moles) and is preferably selected from the group consisting of sodium hypochlorite, sodium hypobromite and Sodium hypochlorite solution having a concentration in the range of 3.2% to 3.6% (1.0-1.2 moles) is most preferred.

In another aspect of the present invention, oxidation is carried out at a temperature between −10° C. to 60° C. preferably 0° C. to 20° C.

Normally acid addition salts or metal salts of organic compounds are more soluble in water and cannot be extracted into solvents, because they are less soluble. But surprisingly we have found that rabeprazole sodium can be extracted from aqueous solution into organic solvents.

In another surprising aspect of the present invention, preparation of rabeprazole sodium incorporates saturation of the aqueous rabeprazole sodium solution by adding inorganic saturating agents like Sodium chloride, followed by extraction using water immiscible solvents like chloroform, dichloromethane, ethylene chloride, ethyl acetate, preferably dichloromethane followed by distillation of the first solvent and addition of the second solvent like ethyl acetate to dissolve the residue and then isolating Rabeprazole sodium by addition of an antisolvent like n-hexane, n-heptane, diisopropyl ether, preferably n-heptane.

Hence the advantages of the above process over the prior art is i) a improved method over the prior art as the current process avoids the use of hazardous solvents. It employs an in situ extractive technology which eliminates the formation of impurities, further abetting reduced unit operations, ecofriendliness and better recovery of the product.

ii) avoiding use of column chromatography iii) a simple process which avoids the isolation and purification of intermediates stages making the present process suitable for industrial applicability.

The following specific examples presented to illustrate the best mode of carrying out the process of the present invention. The examples are not limited to the particular embodiments illustrated herein but include the permutations, which are obvious as set forth in the description.

EXAMPLES

Example 1

Preparation of 2-[[[4-(3-methoxy propoxy)-3-methyl-2-pyridinyl]methyl]-thio]-1H-benzimidazole (Rabeprazole Sulphide)

2-Mercapto benzimidazole (15 g) was suspended in 500 ml Purified water and Sodium hydroxide (8 g). To this was slowly added about 25 g of 2-Chloromethyl-3-methyl-4-(methoxy propoxy)pyridine hydrochloride. The reaction mass was stirred for 2 hours at 20-30° C. and solids were filtered and the wet material can be directly taken up for oxidation or optionally dried in an oven at 45-50° C. to give 31 gm of the title compound.

Example 2

Preparation of 2-[[[4-(3-methoxy propoxy)-3-methyl-2-pyridinyl]methyl]-sulfinyl]-1H-benzimidazole sodium (Rabeprazole Sodium)

2-Mercapto benzimidazole (15 g) was suspended in 500 ml Purified water and Sodium hydroxide (8 g). To this was slowly added about 25 g of 2-Chloromethyl-3-methyl-4-(methoxy propoxy)pyridine hydrochloride. The reaction mass was stirred for 2 hours at 20-30° C. and solids were filtered to obtain 2-[[[4-(3-methoxy-propoxy)-3-methyl-2-pyridinyl]methyl]-thio]-1H-benzimidazole.

The above wet material was suspended in 700 ml Purified Water, Sodium hydroxide (8 g) and Pyridine (17.0 ml). To this 215 g of sodium hypochlorite solution having a chlorine content of 3.2% was slowly added at 5-10° C. in 2 hours. The reaction mass was maintained at 5-8° C. for 2-4 hours. After completion of the reaction, excess sodium hypochlorite was decomposed using 5% aqueous sodium thiosulphate solution. The reaction mass was saturated with about 210 gm of sodium chloride and extracted with 300 ml of dichloromethane twice. The organic layer was dried over Sodium sulphate and concentrated under vacuum to yield a residue.

To this residue, about 200 ml of Ethyl acetate was added and heated to 45-50° C. for 30 mins for dissolution. This solution was then added slowly to about 600 ml of n-Heptane under stirring, filtered under nitrogen atmosphere, washed with 30 ml of n-Heptane and dried in an oven at 45-50° C. to give 28.0 g of the title compound.

Example 3

Preparation of 2-[[[4-(3-methoxy propoxy)-3-methyl-2-pyridinyl]methyl]-sulfinyl]-1H-benzimidazole sodium (Rabeprazole Sodium)

2-[[[4-(3-methoxy-propoxy)-3-methyl-2-pyridinyl]methyl]-thio]-1H benzimidazole (25 g) was suspended in 500 ml of Purified Water, Sodium hydroxide (5 g) and Pyridine (12.5 ml). To this was slowly added about 160 g of Sodium hypochlorite solution having a chlorine content of 3.2% at 5-10° C. in 2 hours. The reaction mass was maintained at 5-8° C. for 2 hours. After completion of the reaction, excess Sodium hypochlorite was decomposed using 5% aqueous Sodium thiosulphate solution. The reaction mass was then saturated with 150 g of Sodium chloride and extracted with 250 ml of dichloromethane twice. The organic layer was then dried over anhydrous Sodium sulphate. Concentrating the organic layer under vacuum yielded a residue to which 125 ml of Ethyl acetate was added and heated to 45-50° C. for dissolution. This solution was slowly added to 500 ml of n-Heptane under stirring and stirred for 2 hours.

The solids were filtered under nitrogen atmosphere, washed with n-Heptane and dried in an oven at 45-50° C. to give 20 g of Rabeprazole sodium.

In view of the above it is evident that the inventors are successful in developing an improved process for the preparation of rabeprazole sodium and rabeprazole sulphide.

The present invention is not to be limited in scope by the specific embodiments described herein. It will be understood that various modifications may be made without departing from the spirit and scope of the invention.

We claim:

1. A process for the preparation of Rabeprazole sodium (2-[[[4-(3-methoxy-propoxy)3-methyl-2-pyridinyl]methyl]-sylfinyl]-1H benzimidazole sodium) comprising the steps of
   a) oxidizing the wet or dry Rabeprazole sulfide (2-[[[4-(3-methoxy-propoxy) 3-methyl-2-pyridinyl]methyl]-thio]-1H benzimidazole of formula (II) with sodium hypohalite solution in water or a mixture of water and water miscible solvent medium using alkali metal hydroxide and a catalyst selected from pyridine, di-isopropyl ethylamine and N,N-dimethylaminopyridine at a temperature range of −10 to 60° C.;
   b) saturating the reaction mass by using sodium chloride,
   c) extracting the sodium salt of rabeprazole using water immiscible organic solvents,
   d) distilling the solvent, dissolving the residue in second organic solvent and precipitating the sodium salt of formula (I) using an antisolvent and
   e) isolating the sodium salt of formula (I).

2. The process as claimed in claim 1, wherein the concentration of said sodium hypohalite solution is 2.0-5.0% of aqueous sodium hypochlorite.

3. The process as claimed in claim 2, wherein said aqueous sodium hypochlorite solution is used in 1-2 moles.

4. The process as claimed in claim 1, wherein said alkali metal hydroxide is 0.5% to 5% Sodium hydroxide.

5. The process as claimed in claim 1, wherein said sodium hydroxide is used in 1.0 to 5.0 moles.

6. The process as claimed in claim 1, wherein said oxidation is carried out at temperature range of 0° C. to 20° C.

7. The process as claimed in claim 1, wherein said water immiscible solvent is selected from chloroform, dichloromethane, ethyl acetate and ethylene chloride.

8. The process as claimed in claim 1, wherein said second solvent used for dissolution is ethyl acetate.

9. The process as claimed in claim 1, wherein said antisolvent is selected from n-Heptane, n-Hexane, and Diisopropyl ether.

10. The process as claimed in claim 1, wherein said water miscible solvent is selected from the group consisting of C1-C4 alcohols, ketones, and nitriles.

* * * * *